US009049865B2

(12) United States Patent  (10) Patent No.: US 9,049,865 B2
Ebbinghaus et al.  (45) Date of Patent: Jun. 9, 2015

(54) USE OF FUNGICIDAL ACTIVE SUBSTANCES FOR CONTROLLING MYCOSES ON PLANTS OF THE PALM FAMILY

(75) Inventors: Dirk Ebbinghaus, Wuppertal (DE); Kerstin Hesse, Bonn (DE); Marie-Claire Grosjean-Cournoyer, Curis Au Mont d Or (FR); David Chamberlin, Marananga (AU)

(73) Assignee: Bayer Intellectual Property GmbH, Monheim (DE)

( * ) Notice: Subject to any disclaimer, the term of this patent is extended or adjusted under 35 U.S.C. 154(b) by 520 days.

(21) Appl. No.: 13/087,144

(22) Filed: Apr. 14, 2011

(65) Prior Publication Data

US 2012/0108580 A1    May 3, 2012

Related U.S. Application Data

(60) Provisional application No. 61/324,066, filed on Apr. 14, 2010.

(30) Foreign Application Priority Data

Apr. 14, 2010  (EP) .................................... 10159882

(51) Int. Cl.
| | |
|---|---|
| A01N 37/52 | (2006.01) |
| A01N 37/50 | (2006.01) |
| A01N 45/02 | (2006.01) |
| A01N 43/88 | (2006.01) |
| A01P 3/00 | (2006.01) |
| A01N 43/653 | (2006.01) |
| A01N 43/40 | (2006.01) |
| A01N 43/56 | (2006.01) |

(52) U.S. Cl.
CPC .............. *A01N 43/653* (2013.01); *A01N 37/50* (2013.01); *A01N 43/40* (2013.01); *A01N 43/56* (2013.01); *A01N 43/88* (2013.01); *A01N 45/02* (2013.01)

(58) Field of Classification Search
CPC ..... A01N 43/88; A01N 43/653; A01N 43/40; A01N 43/56; A01N 37/52; A01P 3/00
USPC ...................................................... 514/229.2
See application file for complete search history.

(56) References Cited

U.S. PATENT DOCUMENTS

| 5,652,354 | A | 7/1997 | Mariani et al. |
| 5,747,518 | A | 5/1998 | Yoshikawa et al. |
| 5,789,566 | A | 8/1998 | Bonhomme et al. |
| 5,859,039 | A | 1/1999 | Jautelat et al. |
| 5,866,782 | A | 2/1999 | Iwabuchi et al. |
| 5,998,450 | A | 12/1999 | Eicken et al. |
| 6,046,382 | A | 4/2000 | Mariani et al. |
| 6,229,072 | B1 | 5/2001 | Burns et al. |
| 2002/0013472 | A1 | 1/2002 | Hillebrand et al. |
| 2002/0032916 | A1 | 3/2002 | Charne et al. |
| 2003/0229087 | A1 | 12/2003 | Mauler-Machnik et al. |
| 2004/0204470 | A1 | 10/2004 | Elbe et al. |
| 2004/0237141 | A1 | 11/2004 | Burns et al. |
| 2005/0101639 | A1 | 5/2005 | Ammermann et al. |
| 2005/0107376 | A1 | 5/2005 | Ammermann et al. |
| 2005/0234110 | A1 | 10/2005 | Mansfield et al. |
| 2007/0066669 | A1 | 3/2007 | Mauler-Machnik et al. |
| 2008/0015244 | A1 | 1/2008 | Dunkel et al. |
| 2008/0070785 | A1 | 3/2008 | Walter et al. |
| 2008/0108686 | A1 | 5/2008 | Gewehr et al. |
| 2008/0148429 | A1 | 6/2008 | Sodhi et al. |
| 2009/0054233 | A1 | 2/2009 | Walter et al. |
| 2009/0069178 | A1 | 3/2009 | Suty-Heinze et al. |
| 2009/0197925 | A1 | 8/2009 | Ehrenfreund et al. |
| 2009/0306109 | A1 | 12/2009 | Dutzmann et al. |
| 2010/0010063 | A1 | 1/2010 | Ehrenfreund et al. |
| 2010/0093715 | A1 | 4/2010 | Voeste et al. |
| 2010/0173966 | A1 | 7/2010 | Stierli et al. |
| 2010/0299779 | A1 | 11/2010 | Primard-Brisset et al. |
| 2011/0112124 | A1 | 5/2011 | Haas et al. |

FOREIGN PATENT DOCUMENTS

| JP | 2000-217581 A | 8/2000 |
| JP | 2001-321194 A | 11/2001 |
| WO | WO 99/16314 A1 | 4/1999 |
| WO | WO 2008129060 A2 * | 10/2008 |

OTHER PUBLICATIONS

Aguín, O., et al, "In vitro selection of an effective fungicide against *Armillariamellea* and control of white root rot of grapevine in the field," *Pest Manag. Sci.* 62:223-228, Society of Chemical Industry, England (2006).
BIOSIS Database, Accession No. PREV198477042799, English language abstract for Alves, M.L.B., et al., "Preliminary tests for the control of black rot of the palm *Bactris-Gasipaes*," *ActaAmazonica* 12:499-502, Instituto Nacional de Pesquisas da Amazônia, Brazil (1982).
BIOSIS Database, Accession No. PREV200200411137, English language abstract for Bloomberg, J.R., et al., "Stratego TM: A new trifloxystrobin-based fungicide for control of rice diseases," *Phytopathology* 92:S148, American Phytopathological Society, United States (2002).
Ferreira, F.A., et al., "Mortality of rooted cuttings of *Pinus* spp. in Brazil caused by *Rhizoctoniasolani*," *Fitopaol. Bras.* 30:201, SociedadeBrasileira de Fitopatlogia, Brazil (2006).
Flood, J., et al., "Studies on oil palm trunks as sources of infection in the field," *Mycopathologia* 159:101-107, Springer (2005).

(Continued)

*Primary Examiner* — Kendra D Carter
*Assistant Examiner* — Jason A Deck
(74) *Attorney, Agent, or Firm* — Sterne, Kessler, Goldstein & Fox P.L.L.C.

(57) ABSTRACT

The present invention relates to the use of specific fungicidal active substances, alone or in combination, for controlling mycoses in plants of the palm family and to a method for using said specific fungicidal active substances for controlling said mycoses in the field of plant protection and the protection of materials.

6 Claims, No Drawings

(56) References Cited

OTHER PUBLICATIONS

Lim, H.P. and Fong, Y.K., "Research on basal stem rot (BSR) of ornamental palms caused by basidiospores from *Ganodermaboninense*," *Mycopathologia* 159:171-179, Springer (2005).

Sanderson, F.R., "An insight into spore dispersal of *Ganodermaboninense* on oil palm," *Mycopathologia* 159:139-141, Springer (2005).

Susanto, A., et al., "Enhancing biological control of basal stem rot disease (*Ganodermaboninense*) in oil palm plantations," *Mycopathologia* 159:153-157, Springer (2005).

Wang, Z.-N., "Three Species of Ganoderma Pathogenic to Macadamia Tree and Their Control," *Rept. Taiwan Sugar Res. Inst.* 129:1-10, Sugar Processing Research Institute, Inc. (1990).

BIOSIS Database, Accession No. PREV199293009314, English language abstract for Wang, Z,-N., "Three Species of Ganoderma Pathogenic to Macadamia Tree and Their Control," *Rept. Taiwan Sugar Res. Inst.* 129:1-10, Sugar Processing Research Institute, Inc. (1990).

European Search Report European Patent Application No. EP 10159882.9, Munich, Germany, mailed on Aug. 5, 2010.

English language Abstract of Japanese Patent Publication No. 2000-217581 A, Japanese Patent Office, Patent & Utility Model Gazette DB, Patent Abstracts of Japan (2000), cited as FP2.

English language Abstract of Japanese Patent Publication No. 2001-321194 A, Japanese Patent Office, Patent & Utility Model Gazette DB, Patent Abstracts of Japan (2001), cited as FP3.

Dialog File 351, Accession No. 2008-H52717, Derwent WPI English language abstract for JP 2008-133237 (2008).

\* cited by examiner

USE OF FUNGICIDAL ACTIVE SUBSTANCES FOR CONTROLLING MYCOSES ON PLANTS OF THE PALM FAMILY

The present invention relates to the use of specific fungicidal active substances, alone or in combination, for controlling mycoses in plants of the palm family and to a method for using said specific fungicidal active substances for controlling said mycoses in the field of plant protection and the protection of materials.

Palms may become infected with fungi via spores, the mycelium or the pseudohyphae of the phytopathogenic fungi. The fungus spreads in the stem via the root system (cf. F. R. Sanderson, Mycopathologia (2005), 159; 139 to 141), which is why the disease is frequently also referred to as "basal stem rot" (BSR). Since this disease is frequently caused by *Ganoderma borinense*, it is also referred to as "*Ganoderma* basal stem rot". A further possibility of infecting is by air-borne spores. Disease strike in the oil palms is of great economic importance in the oil-palm industry in South East Asia and it entails significant yield and stand loss of up to 25% within 6 years (cf. J. Flood et al., Mycopathologia (2005) 159; 101 to 107).

Fungicidal active substances, for example triazoles, carboxamides, strobilurins and their derivatives, are known from the publications DE 103 49 503 A, DE 197 16 257 A, WO 99/16314 A, WO 99/21853 A, WO 96/16048 A, WO 01/84931 A, WO 03/073850 A and WO 03/073852 A. Said active substances and their derivatives are used for controlling phytopathogenic fungi, including those from the division *Basidiomycetes*, inter alia.

However, the use of the abovementioned active substances relates to diseases of cereal crops and non-cereal crops such as grapevines, fruit, peanuts and vegetables. The use of active substance combinations in mycoses on plants of the palm family (Arecaceae) is not known from the abovementioned publications DE 103 49 503 A, DE 19 716 257 A, WO 99/16314 A, WO 99/21853 A, WO 96/16048 A, WO 01/84931 A, WO 03/073850 A and WO 03/073852 A.

WO 2008/129060 A describes a combined method consisting of a fungicidal treatment and transgenic manipulation of crops and vegetable plants in general for controlling mycoses. This method for controlling fungal diseases caused, inter alia, by fungi from the division Basidiomycetes, is also described for the family of the palm plants (Arecaceae), among others. Here, a transgenic manipulation of plants which are subsequently treated with fungicides is capable of reducing the risk of resistance developing. In that publication, a variety of fungicidal active substances, for example triazoles and carboxam ides, are used in conjunction with a transgenic manipulation of the plant to be treated. However, that publication mentions nothing suggesting the use of the fungicidal active substances without transgenic manipulation in plants of the palm family (Arecaceae). It always requires a transgenic manipulation of the abovementioned plants.

US 2009/0069178 A also describes a combination of a treatment with the fungicidal active substances prothioconazole and silthiofam and the use of transgenic manipulations. However, there is no mention of use in plants of the palm family hereinafter in general or in *Elaeis guineensis* oil palms specifically.

JP 2000217581 A and JP 2001321194 A disclose oligonucleotides and a method of detecting, and distinguishing between, phytopathogens of the genus *Ganoderma* in *Elaeis guineensis* oil palms, said method using oligonucleotides. The attack of oil palms by *Ganoderma boninense* can be detected using this method. However, these publications do not refer to the fungicidal control of phytopathogens of the genus *Ganoderma* in diseased oil palms.

Aguin, O. et al. (2006) in Pest Management Science 62:223-228 describe the in vitro selection of fungicides which are active against *Armillaria mellea* and their use for controlling white root rot in grapevines. Triazoles and azoxystrobin are described as effective fungicides. Wang, Z. N. (1990) in Report of the Taiwan Sugar Research Institute 129: 1-10 discloses the use of triadimenol and hexaconazole for controlling *Ganoderma lucidum* in macadamia trees. JP 2008133237 A discloses the use of a composition comprising penthiopyrad for controlling *Rhizoctonia solani* in fruit trees. None of the abovementioned publications mentions the use of the abovementioned fungicides in plants of the palm family hereinafter in general or in *Elaeis guineensis* oil palms specifically.

In conclusion, it can be said that a variety of fungicidal active substances in different combinations are known from the existing prior art for controlling phytopathogens. These fungicidal active substances are employed predominantly in mycoses in cereal plants or vegetable plants and in field-grown fruit. There are no indications in the prior art discussed hereinabove regarding the successful control of mycoses on plants of the palm family, which are specifically adapted to the pests of the latter.

The mechanical or chemical methods known from practice for controlling the fungal pests in plants of the palm family are to date unsatisfactory. Also, the reinfection level of newly-planted plants of the palm family is very high since the fungal pests are capable of persisting, in various stages, stress situations, for example lack of nutrients and temperature effects.

Also, no satisfactory methods have been found to date for controlling fungal diseases and reinfection based on basal stem rot (BSR) disease. This disease has three phases, which are the rot of the seedlings and young plants (1 to 4 years), the rot of the stem base (basal stem rot: from 6 years onwards), and the rot of the upper stem/stalk parts (upper stem rot: from 12 years onwards).

Rot in palms caused by fungi of the genus *Ganoderma* is the most frequent disease and has grave effects on oil palm crops, in particular in Indonesia and Malaysia. Entire plantations may be diseased, which can entail considerable yield reduction and long-term losses as the result of the planting soil being contaminated. The existing control procedure is insufficient for controlling these pests.

A particular danger is the reinfection of newly planted plants in contaminated soils, within which newly-planted plants can become infected within a few months. The first sign of infection is a yellow discoloration of the young shoots/fronds. Infected plants frequently do not develop any fruits and no male flowers until, ultimately, rot becomes visible on the stem and underneath the bark. However, infection does not exclusively occur via the roots. If the palms are pruned during the first 3 to 6 years, it is precisely these pruning sites which are particularly susceptible to infection since the tuft is not fully developed, spores arrive air-borne from various sources and preferentially infect the plant at the pruning sites. The infection becomes visible from fungal fruiting bodies which develop at such pruning sites. These fungal fruiting bodies contain spores. It is in particular the pruning residues left behind in the field, or plant stumps which remain in the soil, which provide a preferred nutrient medium for the fungus, on which fungal fruiting bodies can develop and form a new source of infection. The fungus spreads by colonizing across the mycelium and by pseudohyphae and spreading the spores, and infects young plants. Such a fungal fruiting body can release up to 40 000 spores per minute, which means an enormous risk of infection for the surrounding plants.

Therefore, the currently insufficient control can be attributed to the various states such as the (melanin-containing) mycelium, the basidio spores (spores) and the pseudohyphae of the fungus, by means of which the fungus is capable of persisting through extreme conditions in order to be able to regerminate later under better conditions (cf. Susanto et al., Mycopathologia (2005) 159; 149 to 151). It has been demonstrated that dikaryotic mycelia, too, are capable of infecting plants and causing rot (cf. Lim, H, P; Fong, Y, K, Mycopathologia (2005) 159; 179).

Organic control methods, too, have been the subject of research (cf. Susanto et al. Mycopathologia (2005) 159; 153 to 157). To this end, various bacteria were tested as antagonists, and it has been found that in particular *Trichoderma harzianum, T. viride, Gliocladium viride, Pseudomonas fluorescens* and *Bacillus* sp. are effective against *Ganoderma boninense* in the greenhouse. Oil palms in zones with these antagonists were infected to a lesser degree than oil palms in untreated zones.

In MPOB TT No. 214, June 2004 (ISSN 1511-7871), Idris et al. describe that, compared with benomyl, thiram, triadimefon, triadimenol and tridemorph, bromoconazole and hexaconazole are better suited for prolonging the yield period of *Ganoderma*-infected oil palms.

Nevertheless, the methods known from the prior art for controlling the infection of plants of the palm family with *Ganoderma boninense* are not satisfactory because they are either complicated to carry out or else because the results which are obtained with the treatment methods are insufficient.

Owing to the complexity of the life cycle of phytopathogenic fungi and the variable mode of infection as a function of the age and the stage of the host plants from the plants of the palm family, there is therefore a great need for efficient fungicides which are efficiently active against the various stages of the fungi.

The object of the present invention, therefore, comprises the identification of suitable fungicidal active substances, their derivatives and their combinations for the successful control of mycoses which are caused on plants of the palm family by fungi of the family Ganodermataceae.

It has now been found that the use of one or more fungicidal compounds selected from the group consisting of succinate dehydrogenase inhibitors, triazoles, strobilurins, and mixtures of these are suitable for the successful control of mycoses from the division *Basidiomycetes* in plants of the palm family.

The present invention therefore relates to the use of at least one fungicidal active substance selected from the group consisting of succinate dehydrogenase inhibitors, triazoles, strobilurins, imidazoles, benzotriazines, and pyrionethanil for controlling mycoses from the division *Basidiomycetes*, in particular the family Ganodermataceae, on plants of the palm family.

In a first special embodiment of the present invention, the at least one fungicidal active substance is selected from the group of the succinate dehydrogenase inhibitors, in particular from fluopyram, isopyrazam, boscalid, penthiopyrad, penflufen, sedaxan, fluxapyroxad, bixafen and N-[2-(2,4-dichlorophenyl)-2-methoxy-1-methylethyl]-3-difluoromethyl-1-methyl-1H-pyrazole-4-carboxamide. Within the scope of this first embodiment, the use of bixafen and/or penflufen is especially preferred.

In a second special embodiment of the present invention, the at least one fungicidal active substance is selected from the group of the triazoles. Within the scope of this second embodiment, the use of a fungicidal compound selected from the group consisting of bitertanol, fluquinconazole, prothioconazole and tebuconazole is especially preferred. In a third special embodiment of the present invention, the at least one fungicidal active substance is selected from the group of the strobilurins. Within the scope of this third embodiment, the use of fluoxastrobin and trifloxystrobin is especially preferred.

Preferred within the scope of the present invention is in particular the use of at least one fungicidal active substance selected from the group consisting of prothioconazole, fluquinconazole, bitertanol, tebuconazole, penflufen, bixafen, fluoxastrobin and trifloxystrobin.

In the context of the present invention, succinate dehydrogenase inhibitors are all active substances which have an inhibitory effect on the enzyme succinate dehydrogenase in the mitochondrial respiratory chain. In a preferred embodiment of the present invention, the succinate dehydrogenase inhibitors are selected from the group consisting of fluopyram, isopyrazam, boscalid, penthiopyrad, penflufen, sedaxan, fluxapyroxad, bixafen and N-[2-(2,4-dichlorophenyl)-2-methoxy-1-methylethyl]-3-difluoromethyl-1-methyl-1H-pyrazole-4-carboxamide and of mixtures of these compounds. In an especially preferred embodiment of the present invention, the succinate dehydrogenase inhibitor is bixafen or penflufen.

Bixafen, which has the chemical name N-(3',4'-dichloro-5-fluoro-1,1'-biphenyl-2-yl)-3-(difluoromethyl)-1-methyl-1H-pyrazole-4-carboxamide, and suitable processes for its preparation starting from commercially available starting materials are described in WO 03/070705.

Penflufen, which has the chemical name N-[2-(1,3-dimethylbutyl)phenyl]-5-fluoro-1,3-dimethyl-1H-pyrazole-4-carboxamide, and suitable processes for its preparation starting from commercially available starting materials are described in WO 03/010149.

Fluopyram, which has the chemical name N-{[3-chloro-5-(trifluoromethyl)-2-pyridinyl]ethyl}-2,6-dichlorobenzamide, and suitable processes for its preparation starting from commercially available starting materials are described in EP-A-1 389 614.

Sedaxan is a mixture comprising the two cis isomers of 2'-[(1RS,2RS)-1,1'-bicycloprop-2-yl]-3-(difluoromethyl)-1-methylpyrazole-4-carboxanilide and the two trans isomers of 2'-[(1RS,2SR)-1,1'-bicycloprop-2-yl]-3-(difluoromethyl)-1-methylpyrazole-4-carboxanilide. Sedaxan and suitable processes for its preparation starting from commercially available starting materials are described in WO 03/074491, WO 2006/015865 and WO 2006/015866.

Isopyrazam is a mixture comprising the two syn isomers of 3-(difluoromethyl)-1-methyl-N-[(1RS,4SR,9RS)-1,2,3,4-tetrahydro-9-isopropyl-1,4-methanonaphthalene-5-yl]pyrazole-4-carboxamide and the two anti isomers of 3-(difluoromethyl)-1-methyl-N-[(1RS,4SR,9SR)-1,2,3,4-tetrahydro-9-isopropyl-1,4-methanonaphthalene-5-yl]pyrazole-4-carboxamide. Isopyrazam and suitable processes for its preparation starting from commercially available starting materials are described in WO 2004/035589.

Penthiopyrad, which has the chemical name (RS)—N-[2-(1,3-dimethylbutyl)-3-thienyl]-1-methyl-3-(trifluoromethyl)pyrazole-4-carboxamide, and suitable processes for its preparation starting from commercially available starting materials are described in EP-A-0 737 682.

Boscalid, which has the chemical name 2-chloro-N-(4'-chlorobiphenyl-2-yl)nicotinamide, and suitable processes for its preparation starting from commercially available starting materials are described in DE-A 195 31 813.

Fluxapyroxad, which has the chemical name 3-(difluoromethyl)-1-methyl-N-(3',4',5'-trifluoro-biphenyl-2-yl)-1H-pyrazole-4-carboxamide, and suitable processes for its preparation starting from commercially available starting materials are described in WO 2005/123690.

N-[2-(2,4-Dichlorophenyl)-2-methoxy-1-methylethyl]-3-difluoromethyl-1-methyl-1H-pyrazole-4-carboxamide is usually present as a mixture of 4 stereoisomers. Suitable processes for its preparation starting from commercially available starting materials are described in WO 2008/148570. The stereoisomers (+)-N-[(1R,2S)-2-(2,4-dichlorophenyl)-2-methoxy-1-methylethyl]-3-difluoromethyl-1-methyl-1H-pyrazole-4-carboxamide, (−)-N-[(1S,2R)-2-(2,4-dichlorophenyl)-2-methoxy-1-methylethyl]-3-difluoromethyl-1-methyl-1H-pyrazole-4-carboxamide; (−)-N-[(1R,2R)-2-(2,4-dichlorophenyl)-2-methoxy-1-methylethyl]-3-difluoromethyl-1-methyl-1H-pyrazole-4-carboxamide and (+)-N-[(1S,2S)-2-(2,4-dichlorophenyl)-2-methoxy-1-methylethyl]-3-difluoromethyl-1-methyl-1H-pyrazole-4-carboxamide can be separated from each other for example by HPLC using a chiral stationary phase as described in WO 2010/000612.

The fungicides to be used in accordance with the invention are already known as agrochemical active substances (cf., for example, Pesticide Manual, 15th Edition, November 2009).

The use of the abovementioned fungicides for controlling mycoses from the division *Basidiomycetes* of plants of the palm family has the following advantages over the substances or treatment methods known from the prior art: according to the invention, a good activity is achieved, the active substances provided in accordance with the invention have good ecological and other toxicological properties and have no unacceptable effects on the immediate surrounding of the palm crops.

In the context of the present invention, the mycoses which are controlled within the context of the present invention may also take the form of secondary infections, i.e. that other diseases have already attacked the palm crop before the mycoses.

The active substances provided in accordance with the invention can be used in customary formulations. Thus, the active substance composition can be used for example in the form of a suspension, emulsion, solution, powder, foam, paste, in the form of granules or microparticles, as aerosols or microencapsulations.

The use provided in accordance with the invention of the fungicidal active substances is preferably effected at a dosage rate of between 0.01 and 5 kg/ha, especially preferably between 0.1 and 3 kg/ha, especially preferably between 0.5 and 2 kg/ha.

The fungicidal active substances provided in accordance with the invention are particularly suitable for controlling fungal diseases which spread via the root system of the palm. The active substances provided in accordance with the invention are especially suitable for controlling basal stem rot disease.

Moreover, the use according to the invention also affords general protection from fungal diseases which are transmitted by spores, in particular air-borne spores, the mycelium or the pseudohyphae.

In addition, the use according to the invention is also suitable for protecting against the reinfection of plants of the palm family which have since been freed from microorganisms. Insofar, the use according to the invention can be effected both therapeutically and preventively. Also, effective protection from infection after pruning the palm is possible by the present invention; this applies in particular to any infections via the pruning surface.

It is especially preferred to treat in accordance with the invention palm plants of the palm varieties which are in each case commercially available or in use. However, palm varieties are also understood as meaning palm plants with novel traits which have been bred either by traditional breeding, by mutagenesis or with the aid of recombinant DNA techniques. Within the scope of the present invention, it is also possible to treat palm plants which can be obtained by traditional breeding and optimization methods or else by biotechnological and genetic engineering methods or by combinations of these methods; this includes the transgenic palm plants and the palm plants which are capable or not of being protected by Plant Breeders' Rights.

Within the scope of the present invention, it is also possible to treat genetically modified organisms (GMOs). Genetically modified palm plants (or transgenic palm plants) are plants in which a heterologous gene has been stably integrated into the genome. The expression "heterologous gene" essentially means a gene which has been provided or assembled outside the palm plants and, when introduced into the nuclear, chloroplastic or mitochondrial genome, imparts novel or improved agronomic or other properties to the transformed plant by expressing a protein or polypeptide of interest or by down regulating or silencing another gene which is present in the plant, or other genes which are present in the plant (using, for example, antisense technology, cosuppression technology or RNAi technology [RNA interference]). A heterologous gene that is located in the genome is also called a transgene. A transgene that is defined by its particular location in the plant genome is referred to as a transformation event, or transgenic event.

Palm plants and palm plant varieties which are preferably treated in accordance with the invention include all palm plants which have genetic material which imparts, to these palm plants, especially advantageous, useful traits (whether obtained by breeding and/or by biotechnology).

Palm plants and palm plant varieties which can likewise be treated in accordance with the invention are those palm plants which are resistant to one or more abiotic stress factors. Abiotic stress conditions can include, for example, drought, chill and heat conditions, osmotic stress, water-logging, elevated soil salt content, elevated exposure to minerals, ozone conditions, high-light conditions, limited availability of nitrogen nutrients, limited availability of phosphorus nutrients or the avoidance of shade.

Palm plants and palm plant varieties which can likewise be treated in accordance with the invention are those palm plants which are characterized by enhanced yield characteristics. Enhanced yield in these palm plants can be the result of, for example, improved plant physiology, improved plant growth and improved plant development, such as water utilization efficiency, water retention efficiency, improved nitrogen utilization, improved carbon assimilation, improved photosynthesis, increased germination efficiency and modified maturation. The yield can furthermore be influenced by improved plant architecture (under stress conditions and under non-stress conditions), among which early flowering, flowering control for the production of hybrid seed, seedling vigour, plant size, internode number and distance, root growth, seed size, fruit size, pod size, pod or ear number, number of seeds per pod or ear, seed mass, enhanced seed filling, reduced seed dispersal, reduced pod dehiscence, and lodging resistance. Further yield traits include seed composition, such as carbohydrate content, protein content, oil content and oil composition, nutritional value, reduction in antinutritional compounds, improved processability and improved storability.

Palm plants which can likewise be treated in accordance with the invention are hybrid plants that already express the characteristics of heterosis, or hybrid vigour, which generally results in higher yield, higher vigour, better health and better resistance to biotic and abiotic stress factors. Such plants are typically generated by crossing an inbred male-sterile parent line (the female parent) with another inbred male-fertile parent line (the male parent). The hybrid seed is typically harvested from the male-sterile plants and sold to growers. Male-sterile plants can sometimes (for example in maize) be generated by detasseling (i.e. the mechanical removal of the male reproductive organs or the male flowers); however, more typically, male sterility is the result of genetic determinants in the plant genome. In this case, in particular when seed is the desired product which is to be harvested from the hybrid plants, it is typically useful to ensure that male fertility in hybrid plants which contain the genetic determinants responsible for male sterility is fully restored. This can be achieved by ensuring that the male parents have appropriate fertility restorer genes which are capable of restoring male fertility in hybrid plants which contain the genetic determinants responsible for male sterility. Genetic determinants for male sterility can be located in the cytoplasm. Examples of cytoplasmic male sterility (CMS) have been described for example for *Brassica* species (WO 1992/005251, WO 1995/009910, WO 1998/27806, WO 2005/002324, WO 2006/021972 and U.S. Pat. No. 6,229,072). However, genetic determinants for male sterility may also be located in the nuclear genome. Male-sterile plants can also be obtained by plant biotechnology methods, such as genetic engineering. A particularly advantageous means for generating male-sterile plants is described in WO 89/10396, in which, for example, a ribonuclease such as a barnase is selectively expressed in the tapetum cells in the stamens. The fertility can then be restored by expression in the tapetum cells of a ribonuclease inhibitor such as barstar (for example WO 1991/002069).

Within the context of the present invention, the fungicidal active substance, in its commercially available formulations and in the use forms prepared from these formulations, may be present as a mixture with other active substances such as insecticides, attractants, sterilants, bactericides, acaricides, nematicides, further fungicides, growth-regulating substances, herbicides, safeners and/or fertilizers.

The active substance to be used according to the invention can be used in conventional formulations such as solutions, emulsions, wettable powders, water- and oil-based suspensions and suspension emulsion concentrates.

In the context of the present invention, it is especially preferred when the active substance provided in accordance with the invention is used in the form of a spray formulation.

Suitable formulations and their components are known to the skilled worker per se.

Furthermore, the present invention describes a method of applying the above-described specific fungicidal active substances for controlling said mycoses in the field of plant protection and the protection of materials.

The method according to the invention is characterized in particular by the fact that mycoses can be controlled preventively and/or therapeutically.

The method according to the invention is furthermore particularly characterized in that one or more of the fungicidal active substances specified hereinabove are applied to plants of the palm family, their aerial and/or subterraneous parts, their habitat and/or store and/or their harvested material.

Parts of plants or palm plants of the palm family are understood as meaning aerial and subterraneous plant parts. Subterraneous plant parts are root, rhizomes, tubers, suckers, slips, seeds, seed and soil, and the aerial plant parts include stem, bark, shoot, leaf, flower, fruits, fruiting bodies, stalk, needles, branches. Furthermore, the active substance composition according to the invention can also be applied to the harvested material, the vegetative and the generative propagation material.

The manner of use is variable and can be effected by direct or indirect application to the plant, the environment, the habitat and/or the store. Examples of possible applications which are conceivable are foliar application, seed-dressing products, spraying, spinning, pouring, admixing, scattering, fogging, brushing on, vaporizing, dipping, painting on, coating or applying one or more layers to plant parts. Pressure injection into suitable plants of the palm family is also possible (especially preferred are soil drenching and trunk injection).

For example, the active substance composition can be injected into or below the bark, poured or sprayed around the plant onto the ground (soil, sandy soil, gravelly soil, rocky soil, loamy soil or mixed soil). A further type of application is the spraying onto the plant and its plant parts. In dry form, the active substance composition can be admixed to the ground material (soil, sandy soil, gravelly soil, rocky soil, loamy soil or mixed soil) and/or to the seeds. The active substance composition according to the invention can be applied to the irrigation system, either in dry or else in liquid form. The type of application can be matched individually to the local circumstances and requirements.

As regards further descriptions of the method according to the invention, reference is also made to what has been said hereinabove.

The present invention is suitable for the treatment of any palm crops. Particularly suitable palm crops are palms
(1) of the subfamily Calamoideae:
tribe Eugeissoneae
Eugeissona
tribe Lepidocaryeae
subtribe Ancistrophyllinae (Oncocalamus, Eremospatha and Laccosperma)
subtribe Raphiinae (Raphia)
subtribe Mauritiinae (Lepidocaryum, Mauritia and Mauritiella)
tribe Calameae
subtribe Korthalsiinae (Korthalsia)
subtribe Salaccinae (Eleiodoxa and Salacca)
subtribe Metroxylinae (Metroxylon)
subtribe Pigafettinae (Pigafetta)
subtribe Plectocomiinae (Plectocomia, Myrialepis and Plectocomiopsis)
subtribe Calaminae (rotang palm (Calamus), Retispatha, Daemonorops, Ceratolobus and Pogonotium)
(2) of the subfamily Nypoideae (nipa palm (Nypa))
(3) of the subfamily Coryphoideae
tribe Sabaleae (Sabal)
tribe Cryosophileae (Schippia, Trithrinax, Zombia, Coccothrinax, Hemithrinax, Leucothrinax, Thrinax, Chelyocarpus, Cryosophila and Itaya)
tribe Phoeniceae (date palms (Phoenix))
tribe Trachycarpeae
subtribe Rhapidinae (Chamaerops, Guihaia, hemp palms (Trachycarpus), Rhapidophyllum, Maxburretia and Rhapis)
subtribe Livistoninae (Livistona, ruffled fan palm (Licuala), Johannesteijsmannia, Pholidocarpus and Pritchardiopsis)
inccrtae sedis Trachycarpeae (Acoelorrhaphe, Serenoa, Brahea, Colpothrinax, Copernicia, Pritchardia and Washingtonia)
tribe Chuniophoeniceae (Chuniophoenix, Kerriodoxa, Nannorrhops and Tahina)
tribe Caryoteae (Caryota, Arenga and Wallichia)
tribe Corypheae (Corypha)
tribe Borasseae
subtribe Hyphaeninae (Bismarckia, Satranala, doum palms (Hyphaene) and Medemia)
subtribe Lataniinae (Latania, Lodoicea, Borassodendron and Borassus)
(4) of the subfamily Ceroxyloideae
tribe Cyclospatheae (Pseudophoenix)
tribe Ceroxyleae (Ceroxylon, Juania, Oraniopsis and Ravenea)
tribe Phytelepheae (Ammandra, Aphandra and ivory palms (Phytelephas))
(5) of the subfamily Arecoideae
tribe Iriarteeae (Iriartella, Dictyocaryum, Iriartea, Socratea and Wettinia)
tribe Chamaedoreeae (Hyophorbe, Wendlandiella, Synechanthus, parlour palms (Chamaedorea) and Gaussia)
tribe Podococceae (Podococcus)
tribe Oranieae (Orania)
tribe Sclerospermeae (Sclerosperma)
tribe Roystoneae (Roystonea)
tribe Reinhardtieae (Reinhardtia)
tribe Cocoseae subtribe Attaleinae (Beccariophoenix, Jubaeopsis, Voanioala, Allagoptera, Attalea, jelly palms (Butia), cocos palm (Cocos), honey palm (Jubaea), Lytocaryum, Syagrus and Parajubaea)

subtribe Bactridinae (Acrocomia, Astrocaryum, spiney palms (Aiphanes), Bactris and Desmoncus)

subtribe Elaeidinae (Barcella, oil palms (Elaeis))

tribe Manicarieae (Manicaria)

tribe Euterpeae (Hyospathe, Euterpe, Prestoea, Neonicholsonia and Oenocarpus)

tribe Geonomateae (Welfia, Pholidostachys, Calyptrogyne, Calyptronoma, Asterogyne and Geonoma)

tribe Leopoldinieae (Leopoldinia)

tribe Pelagodoxeae (Pelagodoxa and Sommieria)

tribe Areceae subtribe Archontophoenicinae (Actinorhytis, Archontophoenix, Actinokentia, Chambeyronia and Kentiopsis)

subtribe Arecinae (betel palms (Areca)), Nenga and Pinanga)

subtribe Basseliniinae (Basselinia, Burretiokentia, Cyphophoenix, Cyphosperma, Lepidorrhachis and Physokentia)

subtribe Carpoxylinae (Carpoxylon, Satakentia and Neoveitchia)

subtribe Clinospermatinae (Cyphokentia and Clinosperma)

subtribe Dypsidinae (Dypsis, Lemurophoenix, Marojejya and Masoala)

subtribe Linospadicinae (Calyptrocalyx, Linospadix, Howea and Laccospadix)

subtribe Oncospermatinae (Oncosperma, Deckenia, Acanthophoenix and Tectiphiala)

subtribe Ptychospennatinae (Ptychosperma, Ponapea, Adonidia, Solfia, Balaka, Veitchia, Carpentaria, Wodyetia, Drymophloeus, Normanbya, Brassiophoenix and Ptychococcus)

subtribe Rhopalostylidinae (Rhopalostylis and Hedyscepe)

subtribe Verschaffeltiinae (Nephrosperma, Phoenicophorium, Roscheria and Verschaffeltia)

(6) Incertae sedis Areceae (Bentinckia, Clinostigma, Cyrtostachys, Dictyosperma, Dransfieldia, Heterospathe, Hydriastele, Iguanura, Loxococcus and Rhopaloblaste).

In an especially preferred embodiment of the present invention, the presently described control serves to treat plants of the palm family of the subfamily Arecoideae, furthermore preferably of the tribe Cocosea, even more preferably of the subtribe Elaeidinae. Controlled in particular in the context of the present invention are mycoses on oil palms (Elaeis).

The present invention is explained in greater detail with the aid of the examples which follow.

EXAMPLES

Example 1

I. Description of the Method
1. Culturing of the isolates on potato-dextrose agar (PDA)
2. Preparation of a liquid potato-dextrose broth (PDB) as inoculum For the development of the mycelium, 10 small pieces of the mycelium were transferred into 200 ml of the liquid potato-dextrose broth (PDB) and cultured for 7 days in a greenhouse cabinet at 26° C.

The mycelium was isolated, transferred into 200 ml of fresh liquid potato-dextrose broth supplemented with 25 mg/l enrofloxacin and comminuted using a homogenizer (5 seconds, Ultra Turrax). Thereafter this mycelial suspension was adjusted to two mycelial densities:

Inoculum A: "High mycelial density"
   Homogenized mycelial suspension made up to 400 ml with PDB+enrofloxacin Inoculum B: "Low mycelial density"
   100 ml of inoculum A made up to 400 ml with PDB+enrofloxacin 3. Microtiter plate test:
   Concentration range from 0.0-0.0064-0.032-0.16-4-20 to 100 ppm for each fungicide (active component)
   Fungicide and inoculum were distributed using an automatic dispenser 4. Evaluation (growth determination):
   This is carried out every 2 days (1st evaluation after 4 days) by measuring the absorption over 13 days, using a photometer.

II. Results $EC_{50}$ & ($MEC_{50}$): Fungicide concentration at which the fungal growth is reduced by 50%:

TABLE 1

$EC_{50}$ data [mg/l] of various fungicides, test organism: *G. boninense*-high mycelial density

| $EC_{50}$ data | 1<br>Prothioconazole | 2<br>Fluquinconazole | 3<br>Trifloxystrobin | 4<br>Tebuconazole | 5<br>Bixafen |
|---|---|---|---|---|---|
| *Ganoderma* | | | High density | | |
| *boninense* measurement | | | | | |
| After 6 days | 0.0064 | 0.0365 | 0.0064 | 0.0064 | 0.0854 |
| | 0.0069 | 0.0336 | 0.0064 | 0.0064 | 0.0438 |
| | 0.0087 | 0.0175 | 0.0064 | 0.0064 | 0.0356 |
| | 0.0117 | 0.0407 | 0.0064 | 0.0064 | 0.0350 |
| | 0.0073 | 0.0412 | 0.0064 | 0.0064 | 0.0433 |
| | 0.0064 | 0.0447 | 0.0064 | 0.0064 | 0.0605 |
| $MEC_{50s}$ | 0.008 | 0.034 | 0.006 | 0.006 | 0.070 |
| After 13 days | 0.0064 | 0.0393 | 0.0064 | 0.0064 | 0.1333 |
| | 0.0090 | 0.0450 | 0.0119 | 0.0092 | 0.1283 |
| | 0.0084 | 0.0443 | 0.0081 | 0.0088 | 0.0942 |
| | 0.0120 | 0.0458 | 0.0064 | 0.0126 | 0.0606 |
| | 0.0068 | 0.0352 | 0.0064 | 0.0084 | 0.0818 |
| | 0.0064 | 0.0386 | 0.0115 | 0.0213 | 0.0983 |
| $MEC_{50s}$ | 0.009 | 0.041 | 0.010 | 0.011 | 0.096 |

TABLE 1-continued

EC$_{50}$ data [mg/l] of various fungicides, test organism: *G. boninense*-high mycelial density

| EC$_{50}$ data | 6 Penflufen | 7 Triadimenol | 8 Bitertanol |
|---|---|---|---|
| *Ganoderma* | | High density | |
| *boninense* measurement | | | |
| After 6 days | 0.0076 | 0.0386 | 0.0801 |
|  | 0.0064 | 0.0446 | 0.0518 |
|  | 0.0076 | 0.0475 | 0.0614 |
|  | 0.0098 | 0.0712 | 0.058 |
|  | 0.0087 | 0.0434 | 0.0542 |
|  | 0.008 | 0.0767 | 0.0679 |
| MEC$_{50s}$ | 0.008 | 0.052 | 0.062 |
| After 13 days | 0.0181 | 0.0507 | 0.0389 |
|  | 0.0186 | 0.0582 | 0.0377 |
|  | 0.0154 | 0.059 | 0.0901 |
|  | 0.0305 | 0.1313 | 0.0601 |
|  | 0.0309 | 0.0443 | 0.0498 |
|  | 0.0204 | 0.048 | 0.06 |
| MEC$_{50s}$ | 0.022 | 0.060 | 0.054 |

TABLE 2

EC$_{50}$, data [mg/l] of various fungicides, test organism: *G. boninense*-low mycelial density

| EC$_{50}$ data | 1 Prothio-conazole | 2 Fluoxa-strobin | 3 Fluquin-conazole | 4 Trifloxy-strobin | 5 Tebu-conazole | 6 Bixa-fen |
|---|---|---|---|---|---|---|
| *Ganoderma* | | | Low density | | | |
| *boninense* measurement | | | | | | |
| After 6 days | 0.0064 | 0.0295 | 0.0308 | 0.0064 | 0.0064 | 0.0266 |
|  | 0.0121 | 0.0064 | 0.0178 | 0.0064 | 0.0064 | 0.0188 |
|  | 0.0236 | 0.0562 | 0.0228 | 0.0064 | 0.0064 | 0.0155 |
|  | 0.0163 | 0.0288 | 0.0239 | 0.0064 | 0.0064 | 0.0272 |
|  | 0.0155 | 0.1074 | 0.0224 | 0.0064 | 0.0064 | 0.0537 |
|  | 0.0064 | 0.0614 | 0.022 | 0.0064 | 0.0064 | 0.033 |
| MEC$_{50s}$ | 0.012 | 0.036 | 0.023 | 0.006 | 0.006 | 0.027 |
| After 13 days | 0.0088 | No Fit | 0.0591 | 0.0312 | 0.0086 | 0.1073 |
|  | 0.0115 | 0.2055 | 0.0532 | 0.0064 | 0.0065 | 0.0988 |
|  | 0.0154 | 0.0654 | 0.0915 | 0.1033 | 0.0067 | 0.1464 |
|  | 0.0172 | 0.0502 | 0.0656 | 0.0064 | 0.0072 | 0.1730 |
|  | 0.0217 | 0.4115 | 0.0577 | 0.0861 | 0.0064 | 0.0715 |
|  | 0.0134 | 0.3566 | 0.075 | 0.0064 | 0.0064 | 0.0402 |
| MEC$_{50s}$ | 0.014 | 0.158 | 0.066 | 0.020 | 0.007 | 0.096 |

| EC$_{50}$ data | 7 Penflufen | 8 Triadimenol | 9 Prochloraz | 10 Bitertanol |
|---|---|---|---|---|
| *Ganoderma* | | Low density | | |
| *boninense* measurement | | | | |
| After 6 days | 0.0064 | 0.1063 | 0.4974 | 0.0713 |
|  | 0.0065 | 0.08 | 0.3566 | 0.0477 |
|  | 0.0064 | 0.1062 | 0.5803 | 0.0397 |
|  | 0.0064 | 0.1077 | 0.5515 | 0.0518 |
|  | 0.0064 | 0.1076 | 0.6018 | 0.1062 |
|  | No Fit | 0.0638 | 0.5704 | 0.0682 |
| MEC$_{50s}$ | 0.006 | 0.093 | 0.519 | 0.061 |
| After 13 days | 0.0246 | 0.1032 | 0.9399 | 0.1182 |
|  | 0.0186 | 0.0963 | 0.6978 | 0.1355 |
|  | 0.0306 | 0.0723 | 1.0994 | 0.1360 |
|  | 0.0064 | 0.1064 | 0.7737 | 0.1146 |
|  | 0.0064 | 0.1064 | 0.8261 | 0.1235 |
|  | 0.0228 | 0.1074 | 1.1128 | 0.1014 |
| MEC$_{50s}$ | 0.015 | 0.098 | 0.895 | 0.121 |

Basal stem rot (BSR) disease shows differential sensitivity in respect of the tested components.

As demonstrated by the $EC_{50}$ data ($MEC_{50s}$ in Tables 1 and 2), the growth of *Ganoderma boninense* was inhibited as follows:

Mean $EC_{50}$ data of the active substances from the triazole group:

| | High mycelial density | Low mycelial density |
|---|---|---|
| After 6 days: | | |
| Tebuconazole | 0.006 | 0.006 |
| Prothioconazole: | 0.008 | 0.012 |
| Fluquinconazole | 0.034 | 0.023 |
| Triadimenol | 0.052 | 0.093 |
| Bitertanol | 0.062 | 0.061 |
| After 13 days: | | |
| Tebuconazole | 0.011 | 0.007 |
| Prothioconazole: | 0.009 | 0.014 |
| Fluquinconazole | 0.041 | 0.066 |
| Triadimenol | 0.060 | 0.098 |
| Bitertanol | 0.054 | 0.121 |

The compounds from the triazole group demonstrate excellent efficacy in controlling basal stem rot (BSR) disease. Tebuconazole and prothioconazole showed the best activity, while the activity of fluquinconazole was somewhat lower.

Nevertheless, fluquinconazole proved to be somewhat more effective than triadimenol. In general, the control achieved by triadimenol and bitertanol was similarly effective.

Mean $EC_{50}$ data of the fungicidal active substances from the strobilurin group:

| | High mycelial density | Low mycelial density |
|---|---|---|
| After 6 days: | | |
| Trifloxystrobin: | 0.006 | 0.006 |
| Fluoxastrobin: | | 0.036 |

-continued

| | High mycelial density | Low mycelial density |
|---|---|---|
| After 13 days | | |
| Trifloxystrobin: | 0.010 | 0.020 |
| Fluoxastrobin: | | 0.158 |

Trifloxystrobin revealed an outstanding efficacy in the control of BSR disease. Fluoxastrobin proved to be less effective, with the control by fluoxastrobin having a similarly high efficacy as the control by triadimenol.

Mean $EC_{50}$ data of the fungicidal active substances from the succinate dehydrogenase inhibitor group:

| | High mycelial density | Low mycelial density |
|---|---|---|
| After 6 days: | | |
| Penflufen | 0.008 | 0.006 |
| Bixafen | 0.07 | 0.027 |
| After 13 days | | |
| Penflufen | 0.022 | 0.015 |
| Bixafen | 0.096 | 0.096 |

The appended data demonstrate the detailed efficacies of the various fungicides (dose-effect of the $EC_{50}$ data [mg/l] and document the growth of *Ganoderma boninense* in microtiter plates)

The invention claimed is:

1. A method for controlling mycoses in a plant of the palm family comprising applying a mycoses controlling effective amount of trifloxystrobin to a plant of the palm family in need of said controlling mycoses, wherein said mycoses are from the family Ganodermataceae.

2. The method of claim 1, for controlling mycoses on a palm plant of the subfamily Arecaceae.

3. The method of claim 2, wherein the palm plant of the subfamily Arecaceae belongs to the subtribe Elaeidinae.

4. The method of claim 3, wherein the palm plant is *Elaeis guineensis*.

5. The method of claim 1, comprising applying a composition wherein said composition comprises trifloxystrobin.

6. The method of claim 1, wherein said mycoses can be controlled preventively or therapeutically.

* * * * *